US009691148B2

(12) United States Patent
Fujisawa et al.

(10) Patent No.: US 9,691,148 B2
(45) Date of Patent: Jun. 27, 2017

(54) MEDICAL IMAGING ANALYZER AND MEDICAL IMAGE PROCESSING METHOD

(71) Applicants: Toshiba Medical Systems Corporation, Otawara-shi (JP); Kobe University, Kobe-shi (JP)

(72) Inventors: Yasuko Fujisawa, Nasushiobara (JP); Naoki Sugihara, Nasushiobara (JP); Shigeharu Ohyu, Yaita (JP); Yoshiharu Ohno, Kobe (JP)

(73) Assignees: TOSHIBA MEDICAL SYSTEMS CORPORATION, Otawara-shi (JP); KOBE UNIVERSITY, Kobe-shi (JP)

( * ) Notice: Subject to any disclaimer, the term of this patent is extended or adjusted under 35 U.S.C. 154(b) by 56 days.

(21) Appl. No.: 14/940,789

(22) Filed: Nov. 13, 2015

(65) Prior Publication Data
US 2016/0071271 A1 Mar. 10, 2016

Related U.S. Application Data

(63) Continuation of application No. PCT/JP2014/062738, filed on May 13, 2014.

(30) Foreign Application Priority Data

May 13, 2013 (JP) .................... 2013-101679

(51) Int. Cl.
*G06T 7/00* (2017.01)
*A61B 6/00* (2006.01)
(Continued)

(52) U.S. Cl.
CPC ............ *G06T 7/0016* (2013.01); *A61B 6/481* (2013.01); *A61B 6/486* (2013.01); *A61B 6/507* (2013.01);
(Continued)

(58) Field of Classification Search
CPC combination set(s) only.
See application file for complete search history.

(56) References Cited

U.S. PATENT DOCUMENTS

| 5,150,292 A * | 9/1992 | Hoffmann ............ A61B 6/481 |
| | | 250/303 |
| 6,222,906 B1 * | 4/2001 | Sakaguchi ............ A61B 6/06 |
| | | 257/E27.132 |

(Continued)

FOREIGN PATENT DOCUMENTS

| JP | 2003-210456 A | 7/2003 |
| JP | 2010-068958 A | 4/2010 |

(Continued)

OTHER PUBLICATIONS

International Search Report mailed Jul. 22, 2014 for PCT/JP2014/062738 filed May 13, 2014 with English Translation.

*Primary Examiner* — Anand Bhatnagar
(74) *Attorney, Agent, or Firm* — Oblon, McClelland, Maier & Neustadt, L.L.P.

(57) ABSTRACT

According to one embodiment, a medical imaging analyzer includes an imaging unit, a calculator, and an analyzer. The imaging unit divides an area including an object of a subject to be captured into a plurality of partial areas such that the partial areas overlap each other to form an overlapping area, and administers a contrast agent to each of the partial areas to capture a plurality of time-series images. The calculator calculates, based on the transition of the pixel value in one of the time-series images having the overlapping area, the transition of the pixel value in the other time-series image having the overlapping area. The analyzer analyzes the time-series images based on the transition of the pixel value in the one and the other of the time-series images to obtain the hemodynamics of the subject.

11 Claims, 11 Drawing Sheets

(51) Int. Cl.
  *G06T 11/00* (2006.01)
  *G06T 7/254* (2017.01)
  *A61B 5/055* (2006.01)

(52) U.S. Cl.
  CPC ............ *G06T 7/254* (2017.01); *G06T 11/003* (2013.01); *A61B 5/055* (2013.01); *A61B 2503/22* (2013.01); *A61B 2576/00* (2013.01); *G06T 2207/10088* (2013.01); *G06T 2207/30104* (2013.01)

(56) References Cited

U.S. PATENT DOCUMENTS

| | | | |
|---|---|---|---|
| 8,345,944 B2* | 1/2013 | Zhu | G06K 9/38 378/98.12 |
| 8,792,616 B2* | 7/2014 | Tanaka | A61B 6/0457 378/20 |
| 8,971,600 B2* | 3/2015 | Yoshikawa | A61B 8/06 382/128 |
| 9,433,392 B2* | 9/2016 | Ohishi | A61B 6/463 |
| 2010/0034446 A1* | 2/2010 | Zhu | G06K 9/38 382/130 |
| 2010/0067767 A1* | 3/2010 | Arakita | A61B 6/507 382/131 |
| 2011/0028850 A1* | 2/2011 | Schuhrke | A61B 5/0059 600/476 |
| 2011/0206183 A1* | 8/2011 | Tanaka | A61B 6/0457 378/62 |
| 2013/0225958 A1 | 8/2013 | Ichihara et al. | |
| 2015/0150526 A1* | 6/2015 | Ohishi | A61B 6/463 378/62 |
| 2016/0371836 A1* | 12/2016 | Kuno | G06T 7/0051 |

FOREIGN PATENT DOCUMENTS

| | | |
|---|---|---|
| JP | 2011-172644 A | 9/2011 |
| JP | 2012-090883 A | 5/2012 |

* cited by examiner

MEDICAL IMAGING ANALYZER AND MEDICAL IMAGE PROCESSING METHOD

CROSS-REFERENCE TO RELATED APPLICATION

This application is based upon and claims the benefit of priority from Japanese Patent Application No. 2013-101679, filed 13 May 2013; the entire contents of which are incorporated herein by reference.

FIELD

Embodiments described herein relate generally to a medical imaging analyzer and a medical image processing method.

BACKGROUND

A medical image capturing apparatus such as an X-ray computed tomography (CT) apparatus, a magnetic resonance imaging (MRI) apparatus or the like is used to capture time-series images of a subject to which a contrast agent has been administered to obtain information about the hemodynamics of tissue by analyzing the images. This is called perfusion analysis, which uses the fact that the concentration of the contrast agent in the tissue can be obtained from the value of a pixel corresponding to the tissue in the image.

The time-series images of the subject having been administered a contrast agent are captured by, for example, securing the position of the bed of the apparatus and repeatedly capturing the image of a predetermined area at regular intervals. For example, when the medical image capturing apparatus captures an image 60 times at intervals of 1 second, time-series images of one minute consisting of 60 frames are obtained for the area. The medical imaging analyzer performs the perfusion analysis of the time-series images obtained in this way.

In capturing a large organ such as lung, brain, liver, or the like, the image of an area including the whole organ may not sometimes be captured. Like this, if the organ is larger than the available imaging area per one capturing, a contrast agent is administered to a part of the area of the organ to capture time-series images of the area. This is repeated by moving the bed and securing it again. In other words, a contrast agent is administered more than once, and capturing is performed by moving the imaging area to capture the entire area of the organ in divided areas. The images may be captured such that some areas have an overlapping area.

The breathing or body movement of the subject that occurs during scanning or the movement of the bed may cause a difference in either the shape or size or both of the organ to be rendered in time-series images between one and another of the time-series images. This produces a step in the organ of the subject rendered in the entire image obtained by combining the areas. Incidentally, in general, it takes a long time to capture images for perfusion analysis. As a result, in images captured for perfusion analysis, a large difference is likely to occur in the shape of the organ rendered in the images due to the breathing or body movement during the entire capturing time.

As described above, in the perfusion analysis, the transition is analyzed in the pixel value representing the concentration of a contrast agent administered to capture time-series images. However, when time-series images are captured by moving the imaging area with two or more doses of a contrast agent, the contrast agent administered previous to a particular time-series image may remain in the area represented in the time-series images. The contrast agent administered in the past may also be recirculated and represented in the time-series images. In this case, transition occurs in the concentration of the contrast agent administered to capture the time-series image and that of the contrast agent administered previous to the capturing, and thus the transition of a pixel value representing the sum of the concentrations is analyzed. This reduces the accuracy of the perfusion analysis.

The perfusion analysis requires transition information on the pixel value with respect to an artery to be analyzed. However, in an image captured by capturing divided areas, an artery area may sometimes be specified in only a part of partial image areas. In this case, the perfusion analysis cannot be performed for organ in the partial image where an artery area is not specified.

DETAILED DESCRIPTION

In general, according to one embodiment, a medical imaging analyzer includes an imaging unit, a calculator, and an analyzer. The imaging unit divides an area including an object of a subject to be captured into a plurality of partial areas such that the partial areas overlap each other to form an overlapping area, and administers a contrast agent to each of the partial areas to capture a plurality of time-series images. The calculator calculates, based on a transition in pixel value in one of the time-series images having the overlapping area, a transition in pixel value in another of the time-series images having the overlapping area. The analyzer analyzes the time-series images based on the transition in pixel value in the one and the other of the time-series images to obtain the hemodynamics of the subject.

First Embodiment

Figure 1:
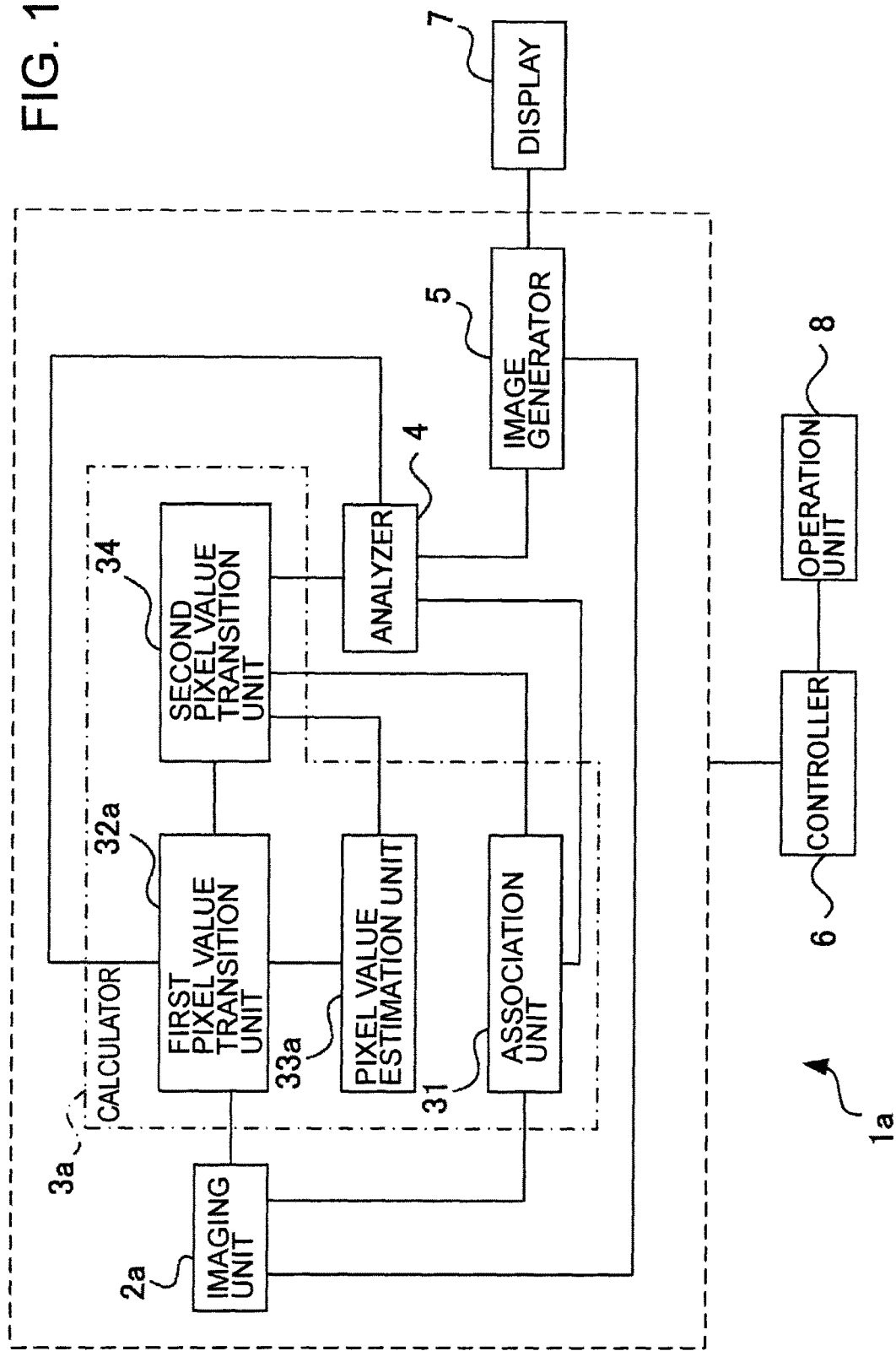
FIG. 1 is a functional block diagram illustrating a configuration of a medical imaging analyzer according to an embodiment.

FIG. 1 is a block diagram illustrating the configuration of a medical imaging analyzer 1a according to a first embodiment. Described below is an example of the configuration of the medical imaging analyzer 1*a*.

Figure 2:
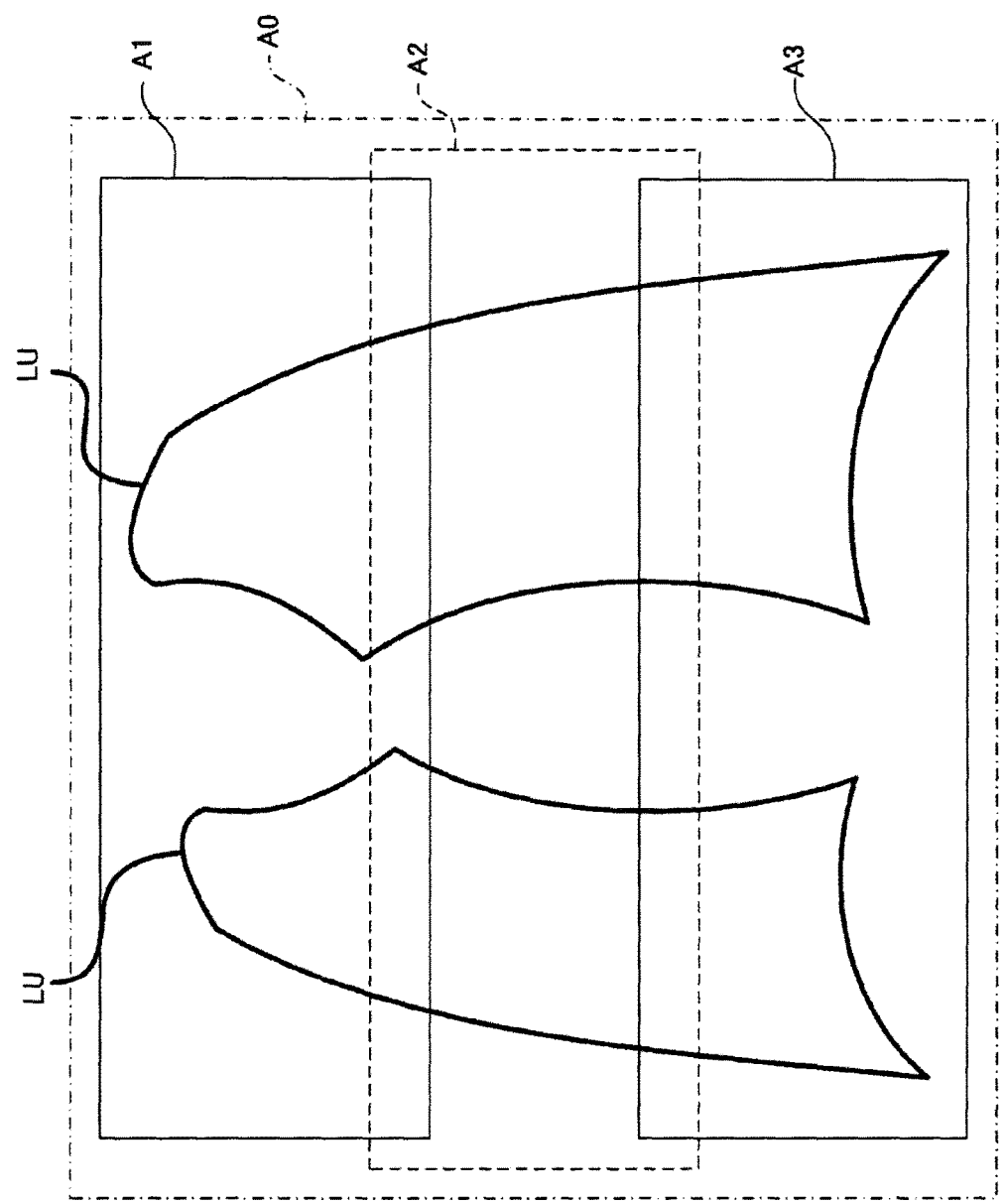
FIG. 2 is a schematic diagram illustrating the outline of the medical imaging analyzer of the embodiment.

An imaging unit 2*a* divides an area including an object of a subject to be captured into a plurality of partial areas such that the partial areas overlap each other to form an overlapping area, and administers a contrast agent to each of the partial areas to capture a plurality of time-series images. For example, the imaging unit 2*a* divides the entire area including a whole site as an object to be captured in the subject into a plurality of partial areas such that adjacent partial areas overlap each other to form an overlapping area. The imaging unit 2*a* administers a contrast agent to each of the partial areas and sequentially captures time-series images with respect to each partial area. Here, the time-series images correspond to a moving image in which a plurality of still images (frames) captured of one area of the subject at regular intervals are correlated in time-series. When a plurality of areas of the subject is captured in time-series, naturally, a plurality of time-series images are obtained. FIG. 2 is a schematic diagram illustrating an example in which a plurality of time-series images is captured of the lungs of the subject as the organ to be analyzed. In this example, time-series images are captured for each of the first area A1, the second area A2 and the third area A3 as partial areas of the entire area A0 including the whole lungs LU. The imaging unit 2*a* outputs the time-series images thus captured to an association unit 31 and a first pixel value transition unit 32*a*. Described below is an example in which the imaging unit 2*a* captures time-series images of the first area A1 of the subject having been administered a contrast agent, the second area A2 of the subject having been administered the contrast agent again, and the third area A3 of the subject after the third administration of the contrast agent. The imaging unit 2*a* acquires a scanned image for determining the locations of a plurality of areas before acquiring the time-series images. As the scanned image, for example, a two-dimensional image is captured based on projection data in the AP direction (0° direction) and LR direction (90° direction). The user designates the locations of the areas to the imaging unit 2*a* while checking the scanned image acquired.

The imaging unit 2*a* may further acquire the entire area image that represents the entire area A0 including a whole target site. Here, the entire area image is a still image of an area including all the first area A1, the second area A2 and the third area A3. For example, the imaging unit 2*a* acquires the entire area image by helical scan or step-and-shoot before the administration of the contrast agent or after the acquisition of the time-series image of the third area. The imaging unit 2*a* outputs the entire area image to the association unit 31.

A calculator 3*a* calculates, based on the transition of the pixel value in one of the time-series images having an overlapping area, the transition of the pixel value in the other time-series image having the overlapping area. The calculator 3*a* includes the association unit 31, the first pixel value transition unit 32*a*, a pixel value estimation unit 33*a*, and a second pixel value transition unit 34.

Having received the time-series images captured, the association unit 31 obtains a correspondence relationship between one and the other of the time-series images, and performs position matching or registration between them. At this time, the association unit 31 obtains a correspondence relationship between the anatomical locations of the time-series images having the same overlapping area. For example, the association unit 31 obtains, as the correspondence relationship, a relationship between the anatomical location of the organ of the subject rendered in an overlapping area in one of the time-series images and that rendered in the same overlapping area in the other time-series image, or scales of them, or the both. Hereinafter, it is referred to as "registration" to associate an image of organ rendered in one of the images with an image of organ rendered in the other based on this correspondence relationship. The one and the other of the time-series images having the same overlapping area correspond to a pair of the time-series images of the first area A1 and the second area A2, and a pair of the time-series images of the second area A2 and the third area A3 in the example of FIG. 2.

Having received the entire area image, the association unit 31 compares the one of the time-series images with the entire area image as well as comparing the other time-series image with the entire area image to obtain the correspondence relationship between time-series images. The association unit 31 performs registration between the one and the other of the time-series images to constitute the entire area image based on the correspondence relationship obtained. At this time, the association unit 31 compares the entire area image with each of the time-series images to obtain the correspondence relationship. The association unit 31 obtains the correspondence relationship between the image of organ rendered in the entire area image and that rendered in each of the time-series images by using, for example, the normalized mutual information (NMI) method or the like. The association unit 31 obtains a correspondence relationship between a partial area in the entire area image, which corresponds to an area a time-series image of which has been captured, and the time-series image. Besides, the association unit 31 may obtain a linear or nonlinear correspondence relationship. For example, the movement of the breathing lungs varies depending on the sites such as the upper lobe and the lower lobe. Therefore, if a linear correspondence relationship is obtained for the time-series images and the entire area image, a difference may occur in the images of organ rendered in them. The association unit 31 can reduce the difference between the image of organ rendered in the time-series images and that in the entire area image by obtaining a nonlinear correspondence relationship. In this way, the correspondence relationship is obtained between the entire area image and each of the time-series images. This means that the time-series images can be registered to each other based on this correspondence relationship. The association unit 31 outputs the correspondence relationship thus obtained to the second pixel value transition unit 34.

When not receiving the entire area image from the imaging unit 2*a*, the association unit 31 compares an image in the overlapping area of one of the time-series images with an image in the overlapping area of the other time-series image to obtain the correspondence relationship between the time-series images. Then, the association unit 31 performs registration between the one of the time-series images and the other time-series image to constitute a target site. The association unit 31 obtains the correspondence relationship between the image in the overlapping area of one of the time-series images and the image in the overlapping area of the other time-series image by using the NMI method or the like. Thereby, the images in their overlapping areas are registered to each other. Further, based on the correspondence relationship thus obtained, the association unit 31 uses the position and the scale as the correspondence relationship for images in areas other than the overlapping area in the time-series images. At this time, the association unit 31 may employ a linear or nonlinear correspondence relationship for the images in the areas other than the overlapping area in the time-series images. When using a linear correspondence relationship for the images in the areas other than the overlapping area in each of the time-series images, the association unit 31 provides the scale and parallel translation of the correspondence relationship obtained. Further, when using a nonlinear correspondence relationship for the images in the areas other than the overlapping area, the association unit 31 applies the amount of parallel translation and the scale different from those in the overlapping area to sites with a larger or smaller movement than that of the overlapping area based on clinical statistical data, for example. The clinical statistical data refers to, for example, data representing a relationship between the movements of the upper and lower lobes of the breathing lungs. The association unit 31 may store the clinical statistical data in advance, or the user may specify the sites while viewing an image of tissue rendered in the image. At this time, the association unit 31 may receive a scanned image from the imaging unit 2a, and obtain a correspondence relationship between a partial area in the scanned image, which corresponds to an area a time-series image of which has been captured, and the time-series image to obtain the correspondence relationship between one of the time-series images and the other time-series image.

Having received the time-series images from the imaging unit 2a, the first pixel value transition unit 32a obtains first pixel value transition information that represents the transition of the pixel value in the time-series images. For example, the first pixel value transition unit 32a obtains the first pixel value transition information as the transition of the pixel value of one of the time-series images that have an overlapping area. The first pixel value transition unit 32a associates pixels of a plurality of frames of the time-series images, and obtains time-series changes in the pixel value of each pixel as the first pixel value transition information. The first pixel value transition information represents a transition in the concentration of the contrast agent in the tissue of the subject corresponding to the pixel. The first pixel value transition unit 32a outputs the first pixel value transition information thus obtained to the pixel value estimation unit 33a and the second pixel value transition unit 34. Incidentally, the graph notation of the first pixel value transition information based on the time axis is referred to as "time density curve".

Further, the first pixel value transition unit 32a obtains artery pixel value transition information that represents changes in the pixel value in an artery area based on the artery area specified in a part of the time-series images. In other words, the first pixel value transition unit 32a obtains pixel value transition information of the concentration of the contrast agent in a position in the subject corresponding to the artery area specified. For example, the first pixel value transition unit 32a calculates the average of pixel values of pixels included in the artery area in each frame, and obtains information on the time-series change of the average as the artery pixel value transition information. The artery area refers to an area that represents a blood inflow pathway to the tissue to be analyzed in the time-series images. There are one or two artery areas. Besides, the lungs have two arteries, i.e., the pulmonary artery and the bronchial artery, as the blood inflow pathway. When the organ is the lungs, generally, it is difficult to specify an area in which the bronchial artery is represented as the artery area. Therefore, an area where the aorta is represented in place of the bronchial artery is specified as the artery area. Incidentally, when the tissue is the brain, an area where the cerebral artery is illustrated is the artery area. When the organ is the liver, an area representing the portal vein as well as an area representing the hepatic artery is the artery area. The first pixel value transition unit 32a outputs the artery pixel value transition information to the analyzer 4.

Since the time-series images are captured by dividing the entire area of the organ into a plurality of areas, the artery area is not always specified in all of them. Accordingly, the artery area is specified in a part of the time-series images, i.e., those of the time-series images captured by capturing a part of the area of the tissue. As a result, the time-series images includes those in which the artery area is specified (time-series images captured by capturing an area that includes the artery area) and those in which the artery area is not specified (time-series images captured by capturing an area that includes no artery area). For example, the user specifies the artery area by using an operation unit 8 while viewing a certain frame. For another example, a first artery pixel value transition information unit may automatically specify the artery area with reference to clinical statistical data.

Figure 3:
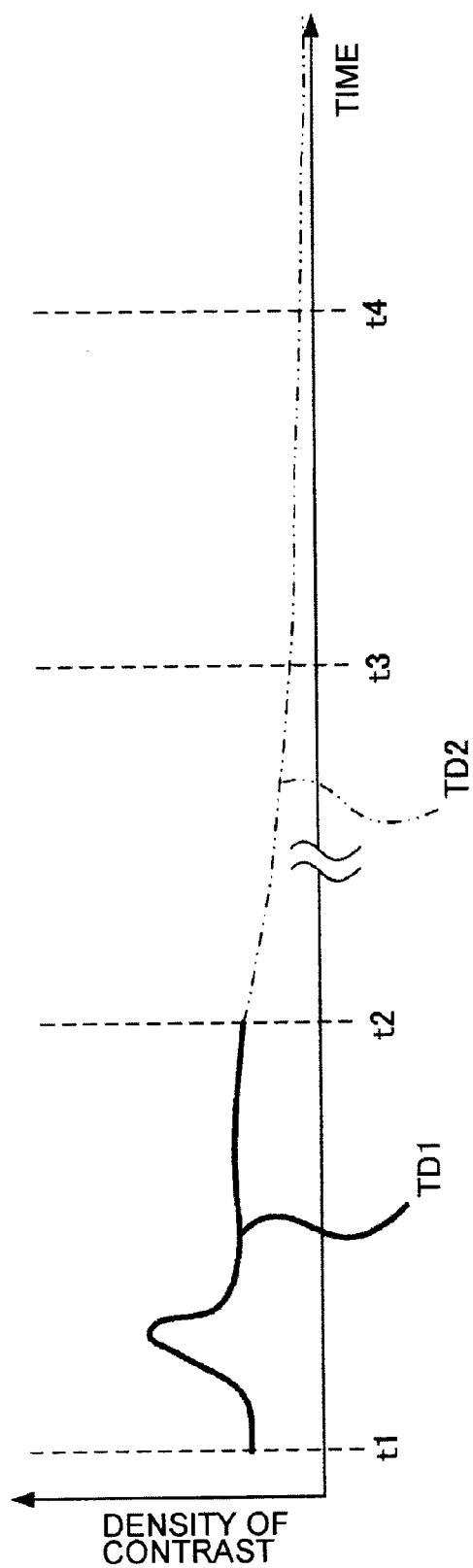
FIG. 3 is a schematic diagram illustrating the outline of the medical imaging analyzer of the embodiment.

Having received the first pixel value transition information, the pixel value estimation unit 33a obtains pixel value estimation information in the overlapping area. The pixel value estimation information is information that, regarding the capturing time of the second and subsequent time-series images among the time-series images related to the first pixel value transition information, estimates the transition of the pixel value due to a change in the concentration of the contrast agent administered for capturing a previous time-series image before the capturing of the current one. FIG. 3 is a schematic diagram illustrating the first pixel value transition information and the pixel value estimation information. The curve TD1 is the time density curve, which is the graph of the first pixel value transition information of the pixel in the overlapping area of the time-series images. Besides, time t1 is the capturing start time of the time-series image, and time t2 is the capturing end time. In other words, the curve TD1 represents the first pixel value transition information from time t1 to time t2. In FIG. 3, the acquisition time of the first pixel value transition information is capturing time from time t1 to time t2. The curve TD2 represents the pixel value estimation information obtained by extrapolating the transition of the pixel after time t2 to the first pixel value transition information represented by the curve TD1. In addition, time t3 is the capturing start time of the next time-series image, and time t4 is the capturing end time. The pixel value transition information represented by the curve TD2 in the capturing time from time t3 to time t4 corresponds to the pixel value estimation information about time-series images captured in the capturing time from the time t3 to the time t4.

The pixel value estimation unit 33a may obtain, for example, the attenuation characteristics of the curve TD1 to obtain the pixel value estimation information. For example, the pixel value estimation unit 33a stores in advance a plurality of attenuation functions that include a damping time constant. The pixel value estimation unit 33a obtains one of the attenuation functions closest to the curve TD1, and obtains the pixel value estimation information based on the damping time constant of the attenuation function obtained. As the attenuation functions, those that monotonically decrease after the predetermined time, such as exponential functions or logarithmic functions, may be set appropriately. The pixel value estimation unit 33a obtains the pixel value estimation information up to the capturing end time of last one of the time-series images, which is captured last (in the example of FIG. 2, the time-series image of the third area A3). The pixel value estimation unit 33a outputs the pixel value estimation information thus obtained to the second pixel value transition unit 34.

Having received the correspondence relationship obtained by the association unit 31, the first pixel value transition information obtained by the first pixel value transition unit 32a, and the pixel value estimation information obtained by the pixel value estimation unit 33a, the second pixel value transition unit 34 obtains second pixel value transition information that represents the transition of the pixel value depending on the concentration of the contrast agent administered to capture each of the time-series images. For example, the second pixel value transition unit 34 obtains the transition of the pixel value in the other of the time-series images having an overlapping area as the second pixel value transition information. The second pixel value transition information represents a transition in the concentration of the contrast agent administered to capture a certain time-series image. In the example of FIG. 2, the second pixel value transition information represents a transition in the concentration of the contrast agent administered to capture the time-series image of the second area A2 (contrast agent by the second administration) and also a transition in the concentration of the contrast agent administered to capture the time-series image of the third area A3 (contrast agent by the third administration).

At this time, the second pixel value transition unit 34 obtains the second pixel value transition information of a time-series image captured later in the time-series images having an overlapping area, based on the pixel value estimation information and the first pixel value transition information of the time-series image, and the correspondence relationship between the time-series image and that captured first. In the example of FIG. 2, the second pixel value transition unit 34 obtains the second pixel value transition information in the time-series image of the second area A2 based on the pixel value estimation information in the time-series image of the first area A1, the first pixel value transition information in the time-series image of the second area A2, and the correspondence relationship between the time-series image of the first area A1 and the time-series image of the second area A2. Further, the second pixel value transition unit 34 obtains the second pixel value transition information in the time-series image of the third area A3 based on the pixel value estimation information in the time-series image of the second area A2, the first pixel value transition information in the time-series image of the third area A3, and the correspondence relationship between the time-series image of the second area A2 and the time-series image of the third area A3.

Figure 4:
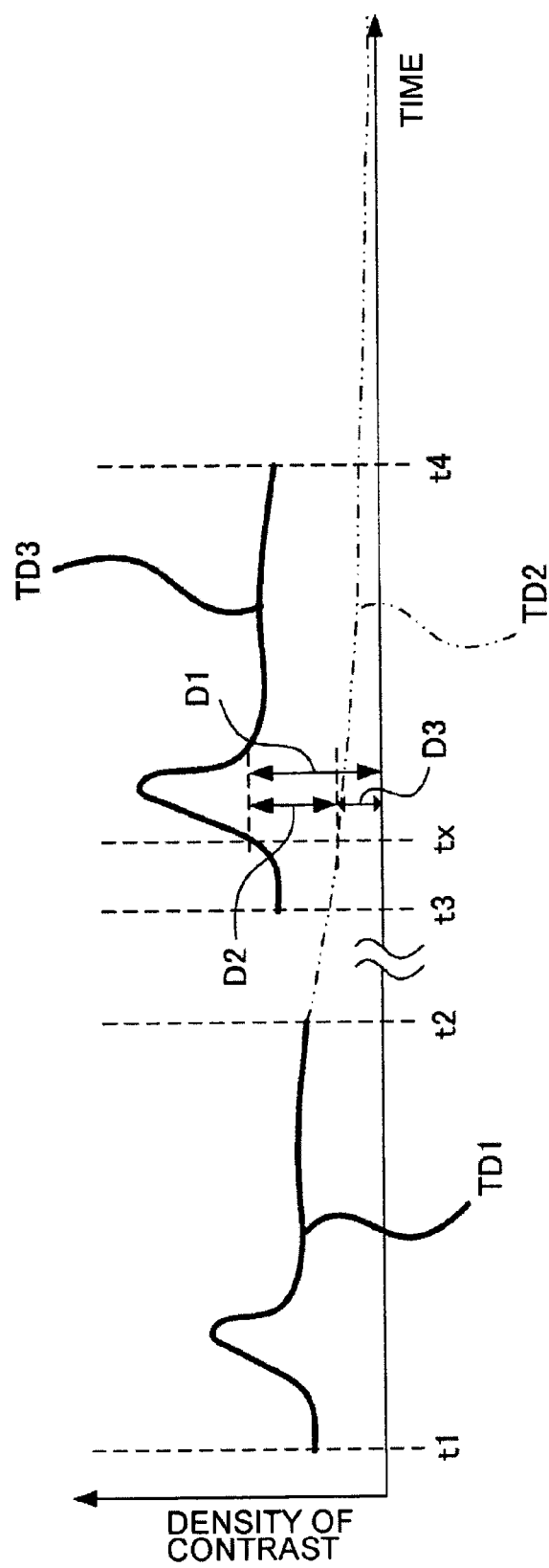
FIG. 4 is a schematic diagram illustrating the outline of the medical imaging analyzer of the embodiment.

For example, the second pixel value transition unit 34 subtracts the pixel value represented by the pixel value estimation information of the time-series image captured later, which has been multiplied by a weighting factor with respect to each time point, from the pixel value represented by the first pixel value transition information of the time-series image captured to obtain the second pixel value transition information. The each time point indicates the time at which each frame of the time-series images are captured. Different weighting factors may be set for individual time points, or the same weighting factor may be set for the time points. The second pixel value transition unit 34 stores in advance the weighting factor(s). The second pixel value transition unit 34 multiplies the pixel value represented by the pixel value estimation information by the weighting factor, and subtracts the resultant value from the pixel value represented by the first pixel value transition information. The weighting factor may be entered by the user. FIG. 4 is a schematic diagram illustrating the time density curve TD1 representing the first pixel value transition information of a time-series image captured first, and the capturing start time t1 and the capturing end time t2 of the time-series image, the time density curve TD3 representing the first pixel value transition information of a time-series image captured later, and the capturing start time t3 and the capturing end time t4 of the time-series image, and the curve TD2 representing the pixel value estimation information included in the time-series images with respect to pixels in the overlapping area between the time-series images. For example, the concentration D1 is obtained as the pixel value transition information, which is the concentration of the contrast agent including both the concentration D2 of the contrast agent administered at the time tx of the first pixel value transition information represented by the curve TD3 to capture the time-series image, and the concentration D3 of the contrast agent at the time tx of the curve TD2 representing the residual and recycled components of the contrast agent administered to capture time-series images from time t1 to time t2. The concentrations D2 and D3 change individually. The second pixel value transition unit 34 multiplies, for example, the pixel value represented by the curve TD2 for each time point from time t3 to time t4 by a weighting factor, and subtracts the resultant value from the pixel value represented by the curve TD3. For example, at a time point where the weighting factor is "1", the second pixel value transition unit 34 subtracts the pixel value representing the concentration D3 at the time point from the pixel value representing the concentration D1 at that time. For another example, at a time point where the weighting factor is "0.8", the second pixel value transition unit 34 subtracts 0.8 times the pixel value representing the concentration D3 at the time point from the pixel value representing the concentration D1 at that time. Besides, when the same weighting factor is set for each time point, the second pixel value transition unit 34 multiplies the pixel value representing the concentration D3 by the same weighting factor at each time point from time t3 to time t4, and subtracts the resultant value from the pixel values representing the density D1. Thereby, the second pixel value transition unit 34 can correct the influence of the residual and recycle components of the contrast agent administered to capture previous time-series images before the capturing of the current one for time-series images captured after a plurality of times of administration of the contrast agent (in the example of FIG. 2, for the time-series image of the second area A2 and the time-series image of the third area A3). Besides, if the artery area is set in the overlapping area, the analyzer 4 (described later) may obtain an input function for the time-series images captured after a plurality of times of administration of the contrast agent. The second pixel value transition unit 34 outputs the second pixel value transition information thus obtained to the analyzer 4.

The analyzer 4 analyzes the time-series images to obtain the hemodynamics of the subject. For example, the analyzer 4 analyzes the time-series images based on the transition of the pixel value of one and the other of the time-series images having an overlapping area to obtain the hemodynamics of the subject. The analyzer 4 performs perfusion analysis on each of the time-series images according to a specified analysis method based on the correspondence relationship from the association unit 31, the first pixel value transition information from the first pixel value transition unit 32a, the second pixel value transition information from the second pixel value transition unit 34. Examples of the analysis method include deconvolution method and maximum slope method. The user may specify the analysis method using the operation unit 8, or it may be preset in the analyzer 4.

The analyzer 4 performs perfusion analysis on a time-series image, where an artery area is specified, among the time-series images using the artery pixel value transition information of the time-series image as an input function according to an analysis method specified with respect to pixels in areas other than the artery area in the time-series image. Here, among the time-series images, when an artery area is specified in time-series images captured by administering a contrast agent a plurality of times (in the example of FIG. 2, the time-series image of the second area A2 and the time-series image of the third area A3), the analyzer 4 performs perfusion analysis using the second pixel value transition information of pixels in the artery area as an input function. The input function represents a transition in the concentration of the contrast agent, which has been administered to capture the time-series images, in the artery area.

Described below is an example in which the analyzer 4 obtains the input function for those of the time-series images where an artery area is not specified. At this time, the analyzer 4 selects, for example, vessel pixels each representing a blood vessel from pixels of the time-series images. As a method for selecting a vessel pixel, for example, the analyzer 4 creates a graph of blood vessels of the tissue, and obtains a branch point in the graph. The analyzer 4 performs a distance transform in a certain area in the vicinity of the branch point, and obtains a product set area regarding each branch in the certain area as a cylinder. The analyzer 4 selects a pixel corresponding to the center of gravity of the product set area as a vessel pixel. This selection is performed with respect to overlapping areas.

Figure 5:
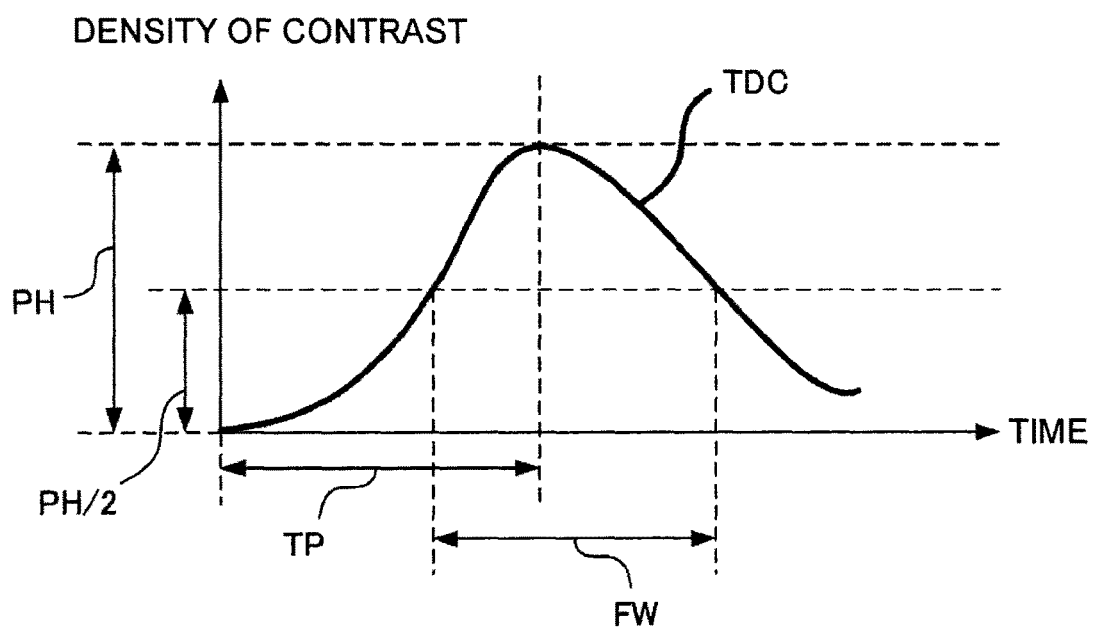
FIG. 5 is a schematic diagram illustrating the outline of the medical imaging analyzer of the embodiment.

The analyzer 4 stores in advance blood vessel classification information that represents the characteristics of each type of blood vessel. The analyzer 4 determines the type of the blood vessel represented by the vessel pixels based on the second pixel value transition information of the selected vessel pixels and the vessel classification information. The analyzer 4 includes the blood vessel type thus determined in the vessel pixel value transition information to obtain the second vessel pixel value transition information. The blood vessel classification information is, for example, information that represents the characteristics of the time density curve of each blood vessel type such as the pulmonary artery and the bronchial artery. FIG. 5 is a schematic diagram illustrating an example of the characteristics of a time density curve TDC. Examples of the characteristics of the time density curve TDC include peak height (PH), curve width (full width at half maximum: FW), peak time (time to peak: TP) and the like. In FIG. 5, "PH/2" indicates a contrast concentration of half of that at the peak height PH. These characteristics are known to be different among blood vessel types. The analyzer 4 compares the blood vessel classification information stored in advance with the time density curve of the vessel pixel value transition information to determine the type of the blood vessel represented by the vessel pixel of the vessel pixel value transition information. For example, if the lungs are to be analyzed, the analyzer 4 determines the type of each blood vessel represented by the vessel pixels as the pulmonary artery, the bronchial artery, or another type (neither the bronchial artery nor the pulmonary artery).

Here, since the analyzer 4 has performed perfusion analysis on the time-series image where an artery area is specified, in the time-series image, a correlation has been obtained between the input function and the first pixel value transition information or the second pixel value transition information of the vessel pixel. Further, the analyzer 4 obtains a pixel corresponding to the vessel pixel of the time-series images where an artery area is specified from among vessel pixels of the time-series images where an artery area is not specified based on the correspondence relationship. At this time, from among the vessel pixels in the overlapping area, the analyzer 4 obtains a pixel corresponding to the vessel pixel determined to be of the pulmonary artery or the bronchial artery. The pixel thus obtained is a vessel pixel in time-series images where an artery area is not specified, and represents substantially the same blood vessel as that represented by vessel pixels in the time-series images where an artery area is specified. The analyzer 4 applies a correlation between the input function and the first pixel value transition information or the second pixel value transition information of the vessel pixel in the time-series images where an artery area is specified to a vessel pixel, which is a pixel corresponding to the vessel pixel, in the time-series images where an artery area is not specified to determine the input function of the time-series images where an artery area is not specified. Hereinafter, the input function is referred to as "estimated input function". Thus, the analyzer 4 performs perfusion analysis for the input function and each pixel of the time-series images where an artery area is not specified.

Further, the analyzer 4 performs perfusion analysis for the time-series image captured first (in the example of FIG. 2, the time-series image of the first area A1) based on the first pixel value transition information obtained by the first pixel value transition unit 32a to obtain the hemodynamics of the tissue of the subject corresponding to each pixel. The analyzer 4 performs perfusion analysis for a time-series image captured of the subject having been administered the contrast agent a plurality of times (in the example of FIG. 2, the time-series images of the second area A2 and the time-series image of the third area A3) based on the second pixel value transition information obtained by the second pixel value transition unit to obtain the hemodynamics. When an artery area is specified in the time-series image captured of the subject having been administered the contrast agent a plurality of times, the analyzer 4 uses the average of the second pixel value transition information corresponding to the artery area as an input function. Thereby, the analyzer 4 can perform perfusion analysis, for each of the time-series images, with respect to the pixel value transition information that represents a transition in the concentration of the contrast agent administered to capture the time-series image. In this way, the analyzer 4 obtains the hemodynamics for each of the time-series images, and outputs it to an image generator 5. The hemodynamics includes, for example, the blood-flow volume, average transit time, blood volume, and the like.

Having received the hemodynamics obtained by the analyzer 4, the image generator 5 generates a map that represents the hemodynamics of the organ of the subject. Examples of the map include a blood-flow volume map and a blood volume map which represent the blood-flow volume and blood volume of the organ of the lungs, respectively.

At this time, upon receipt of the hemodynamic obtained by the analyzer 4, the time-series images, and the correspondence relationship, the image generator 5 performs weighted addition of the hemodynamics of one and the other of the time-series images having an overlapping area. The image generator 5 is capable of registration between the time-series images based on the correspondence relationship received. In the overlapping area, the hemodynamics is obtained in one and the other of the time-series images. The image generator 5 generates a map that represents the hemodynamics in the overlapping area and other areas continuously by the weighted addition of the hemodynamics of both the time-series images.

For example, having received the time-series images from the imaging unit 2a, the image generator 5 obtains the difference between the pixel values of the time-series images having an overlapping area based on a previous time-series image captured first as a reference. The image generator 5 calculates a weighting factor based on the difference to correct the hemodynamics of the time-series image captured later. Besides, for example, when each of the time-series images contains a blood vessel in which the blood-flow volume does not change, in response to the designation of the blood vessel, the image generator 5 calculate a weighting factor with reference to the pixel value corresponding to the blood vessel. For example, when each of the time-series images contains the aorta, the blood-flow volume of the aorta can be considered as unchanged during perfusion imaging. The image generator 5 calculates the weighting factor for each of the time-series images such that the hemodynamics of the aorta rendered in one of the time-series images is equal to the hemodynamics of the aorta rendered in the other time-series image to correct the hemodynamics. The image generator 5 displays, on a display 7, an entire area map obtained by joining hemodynamics maps, which have been corrected with respect to each area.

A controller 6 controls each unit. The controller 6 includes, for example, a storage and a processor (not illustrated). The storage stores computer programs for implementing the functions of each unit of the medical imaging analyzer 1a. The processor executes the computer programs to implement the above functions.

The display 7 is a display device formed of, for example, a cathode ray tube (CRT) or a liquid crystal display (LCD). The display 7 is not necessarily provided as integrated with the medical imaging analyzer 1a, and may be configured to display images via a common interface.

While being operated by the user, the operation unit 8 feeds each unit of the apparatus with a signal and information corresponding to the content of the operation. The operation unit 8 includes, for example, a keyboard, a mouse, a touch panel, and the like. The operation unit 8 is not necessarily provided as integrated with the medical imaging analyzer 1a, and may be configured to feed the signal and information to each unit of the apparatus via a common interface.

Figure 6:
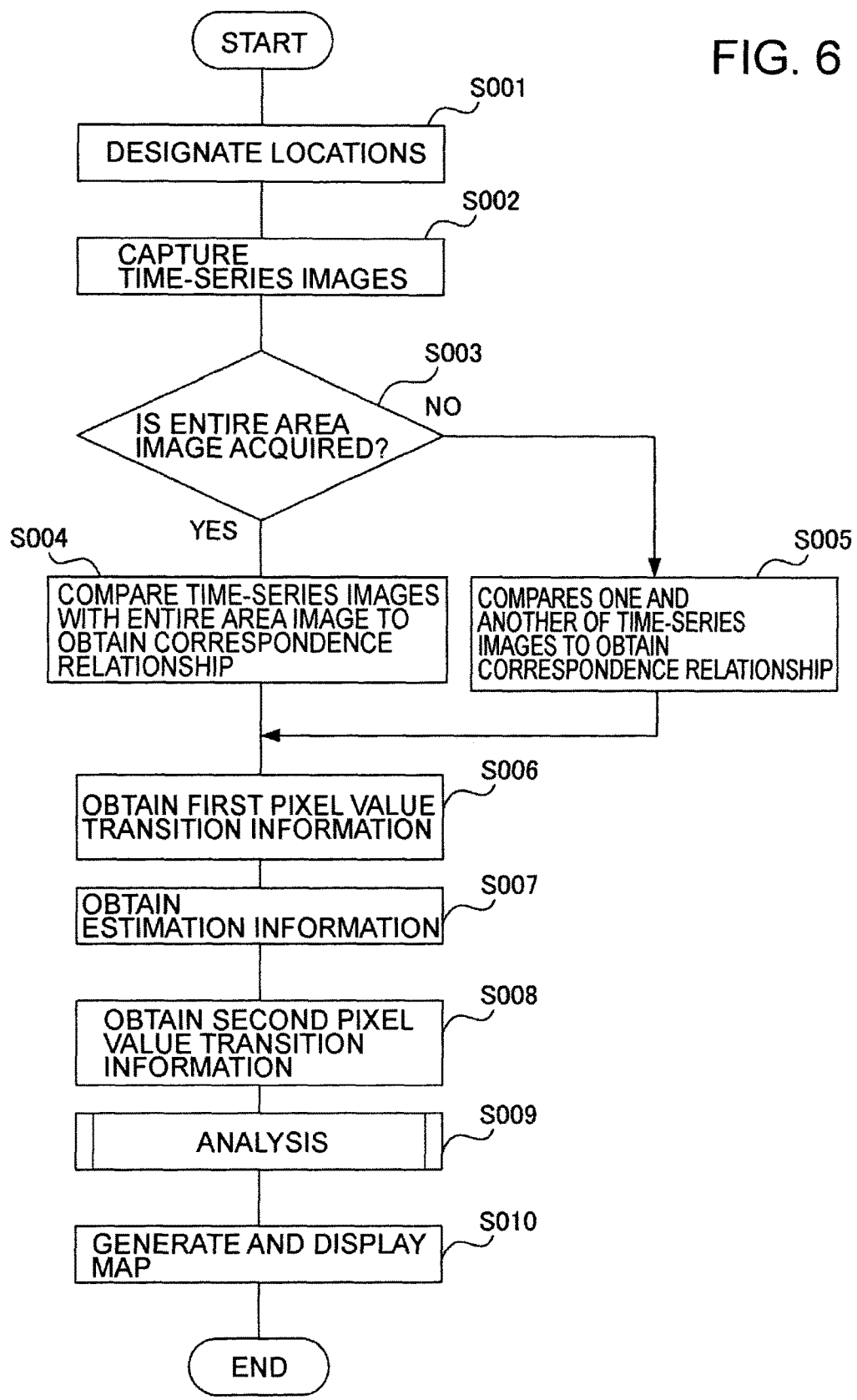
FIG. 6 is a flowchart of an example of the operation of the medical imaging analyzer of the embodiment.

FIG. 6 is a flowchart illustrating the operation of the medical imaging analyzer 1a of this embodiment. Described below is the operation of the medical imaging analyzer 1a.

S001: The imaging unit 2a obtains a scanned image, and receives the designation of the locations of a plurality of areas. The imaging unit 2a may acquire an entire area image that represents all the areas of a subject.

S002: The imaging unit 2a divides an area including an object of the subject to be captured into a plurality of partial areas such that the partial areas overlap each other to form an overlapping area, and administers a contrast agent to each of the partial areas to capture a plurality of time-series images. At this time, the imaging unit 2a captures time-series images of a plurality of areas of the subject having an overlapping area, which have been administered a contrast agent at different times. When a plurality of areas of the subject is captured in time-series, naturally, a plurality of time-series images are obtained. Incidentally, after capturing the time-series images, the imaging unit 2a may acquire an entire area image that represents all the areas of the subject. Step S002 corresponds to one example of "capturing" in this embodiment.

S003: If the entire area image is acquired, the process moves to step S004. If not, the process moves to step S005.

S004: Having received the entire area image, the association unit 31 compares the one of the time-series images with the entire area image as well as comparing the other time-series image with the entire area image to obtain the correspondence relationship between time-series images.

S005: When not receiving the entire area image from the imaging unit 2a, the association unit 31 compares an image in the overlapping area of one of the time-series images with an image in the overlapping area of the other time-series image to obtain the correspondence relationship between the time-series images.

S006: Having received the time-series images from the imaging unit 2a, the first pixel value transition unit 32a obtains first pixel value transition information that represents the transition of the pixel value in the time-series images. Here, the first pixel value transition unit 32a associates pixels of a plurality of frames of the time-series images, and obtains time-series changes in the pixel value of each pixel as the first pixel value transition information. Besides, the first pixel value transition unit 32a obtains artery pixel value transition information for those of the time-series images where an artery area is specified.

S007: Having received the first pixel value transition information, the pixel value estimation unit 33a obtains pixel value estimation information for each pixel. The pixel value estimation information is information that estimates a transition in the concentration of the contrast agent in the overlapping area, which is represented by the pixel value of the time-series images related to the first pixel value transition information, after the time of the first pixel value transition information.

S008: Having received correspondence relationship obtained by the association unit 31, the first pixel value transition information obtained by the first pixel value transition unit 32a, and the pixel value estimation information obtained by the pixel value estimation unit 33a, the second pixel value transition unit 34 obtains second pixel value transition information that represents the transition of the pixel value due to the concentration of the contrast agent administered for capturing each of the time-series images.

Steps S004, S005, S006, S007 and S008 correspond to one example of "calculating" in this embodiment.

S009: Having received the time-series images, the analyzer 4 performs perfusion analysis on each of the time-series images. Details of this perfusion analysis are described later. Step S009 corresponds to one example of "analyzing" in this embodiment.

S010: Having received the hemodynamics obtained by the analyzer 4, the image generator 5 generates a map that represents the hemodynamics of the tissue of the subject for the entire area of the plurality of areas. The image generator 5 displays the map on the display 7.

Figure 7:
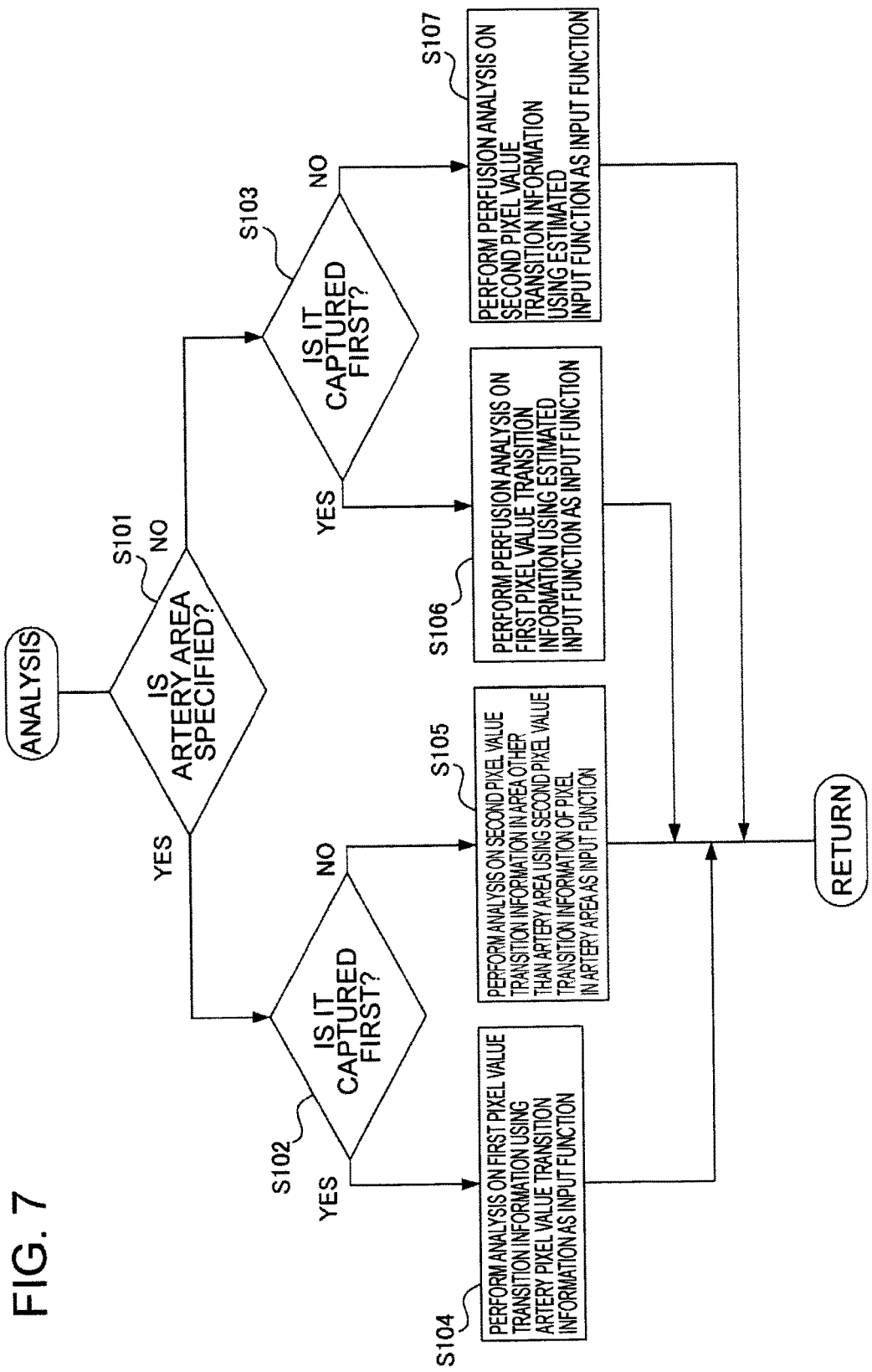
FIG. 7 is a flowchart of an example of the operation of the medical imaging analyzer of the embodiment.

With reference to FIG. 7, the perfusion analysis is described in detail.

S101: When an artery area is specified in the time-series images, the process proceeds to step S102. When no artery area is specified in the time-series images, the process proceeds to step S103.

S102: When the time-series image is the one captured first, the process proceeds to step S104. When the time-series image is not the first one, the process proceeds to step S105.

S103: When the time-series image is the one captured first, the process proceeds to step S106. When the time-series image is not the first one, the process proceeds to step S107.

S104: The analyzer 4 performs perfusion analysis on the first pixel value transition information of the pixel value in an area other than the artery area in the time-series images using the artery pixel value transition information as an input function to obtain the hemodynamics. The analyzer 4 outputs the hemodynamic thus obtained to the image generator 5.

S105: The analyzer 4 performs perfusion analysis on the second pixel value transition information of the pixel value in an area other than the artery area in the time-series images using the second pixel value transition information of the pixel in the artery area as an input function to obtain the hemodynamics. The analyzer 4 outputs the hemodynamic thus obtained to the image generator 5.

S106: The analyzer 4 obtains an estimated input function for the time-series images where an artery area is not specified. The analyzer 4 performs perfusion analysis on the first pixel value transition information of the pixel value of the pixel in the time-series images using the estimated input function as an input function to obtain the hemodynamics. The analyzer 4 outputs the hemodynamic thus obtained to the image generator 5.

S107: The analyzer 4 obtains an estimated input function for the time-series images where an artery area is not specified. The analyzer 4 performs perfusion analysis on the second pixel value transition information of the pixel value of the pixel in the time-series images using the estimated input function as an input function to obtain the hemodynamics. The analyzer 4 outputs the hemodynamic thus obtained to the image generator 5.

According to the first embodiment, the medical imaging analyzer 1a includes the imaging unit 2a configured to capture a plurality of time-series images of a plurality of areas of a subject having an overlapping area, which have been administered a contrast agent at different times, and the analyzer 4 configured to analyze the time-series images to obtain hemodynamics of the subject. The medical imaging analyzer 1a includes the association unit 31, the first pixel value transition unit 32a, the pixel value estimation unit 33a, and the second pixel value transition unit 34. The association unit 31 is configured to receive the time-series images, and obtain a correspondence relationship between one and another of the time-series images having the same overlapping area. The first pixel value transition unit 32a is configured to obtain first pixel value transition information that represents a transition in pixel value in the time-series images. The pixel value estimation unit 33a is configured to receive the first pixel value transition information, and obtain pixel value estimation information, which estimates a transition in concentration of the contrast agent in the overlapping area, which is represented by pixel value of the time-series images related to the first pixel value transition information, after time of the first pixel value transition information. The second pixel value transition unit 34 is configured to receive the correspondence relationship obtained by the association unit 31, the first pixel value transition information obtained by the first pixel value transition unit 32a, and the pixel value estimation information obtained by the pixel value estimation unit 33a, and obtain second pixel value transition information that represents a transition in pixel value due to the concentration of the contrast agent administered to capture each of the time-series images. In this manner, the medical imaging analyzer 1a performs registration between a plurality of time-series images, and obtains pixel value transition information on the concentration of the contrast agent administered to capture each of the time-series images. The medical imaging analyzer 1a performs perfusion analysis based on the input function for each of the time-series images. Then, the medical imaging analyzer 1a generates a hemodynamics map of the entire area by combining hemodynamics obtained with respect to each of the time-series images continuously, and displays it. This enables to reduce the difference in the shape and size of the organ to be rendered in images captured by moving the imaging area with a plurality of administrations of a contrast agent as well as to reduce the effect of residual contrast agent. Thus, it is possible to perform perfusion analysis on an image in which an artery area is not specified.

Second Embodiment

Figure 8:
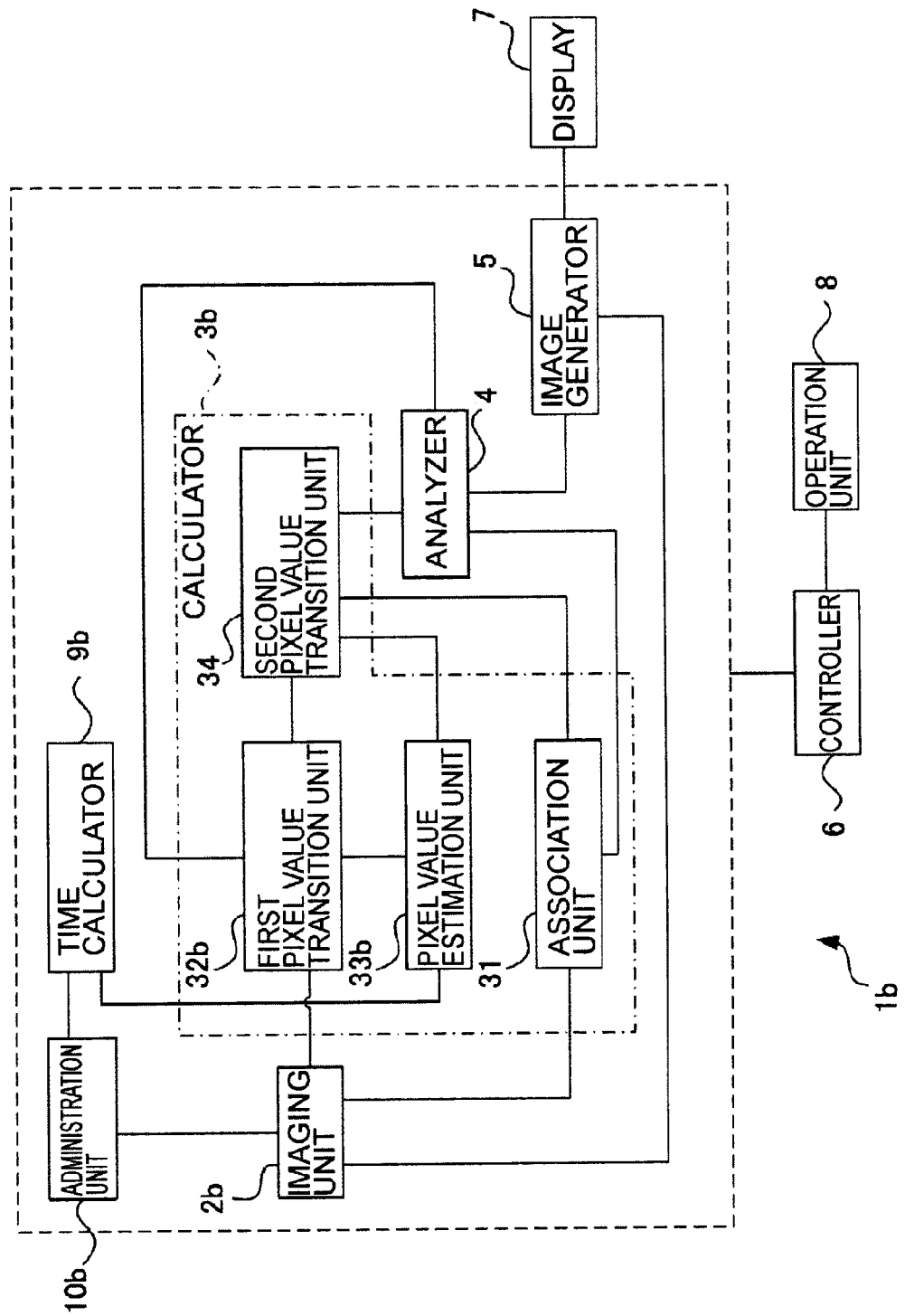
FIG. 8 is a functional block diagram illustrating a configuration of a medical imaging analyzer according to another embodiment.

FIG. 8 is a block diagram illustrating a configuration of a medical imaging analyzer 1b of this embodiment. The medical imaging analyzer 1b of this embodiment includes, in addition to the configuration of the medical imaging analyzer 1a of the first embodiment, a time calculator 9b and an administration unit 10b. Described below are the differences from the medical imaging analyzer 1a of the first embodiment.

Each time time-series images are captured with respect to one area, the time calculator 9b receives pixel value estimation information and calculates the time to start administering a contrast agent to capture the next time-series images. Generally, as indicated by the curve TD2 in FIG. 3, the concentration of the contrast agent tends asymptotically to a low value such as zero or the like. Accordingly, the curve TD2 representing the graph of the pixel value estimation information has a tangent line the slope of which is asymptotic to zero. The time calculator 9b stores in advance a threshold value for this slope. The time calculator 9b also obtains a correlation between the time and slope of the time density curve based on the pixel value estimation information, and calculates the time at which the slope is equal to or less than the threshold value as administration start time. The time calculator 9b performs this calculation for an overlapping area that overlaps the area of a time-series image to be captured next. Here, as the pixel value estimation information of the overlapping area is asymptotic to a low value, less components of the contrast agent remains in the time-series image to be captured next. That is, the time calculator 9b calculates the time at which the contrast agent administered for captured time-series images less remains in time-series images to be captured next. The time calculated by the time calculator 9b as the administration start time, i.e., the level to which the contrast agent reduces, may be designed by the threshold value stored in advance. The time calculator 9b may calculate the administration start time as, for example, a time based on the time scale used in daily life. The time calculator 9b outputs the administration start time to the administration unit 10b.

Having received the administration start time thus calculated, the administration unit 10b administers a contrast agent to a subject based on the administration start time. For example, the administration unit 10b includes a clock, and when it reaches the time of the calculation result received, the administration unit 10b administers a contrast agent to a subject (automatic administration). The contrast agent administered at this time is the one to capture time-series images of the next area. Incidentally, the mechanism of a typical injector may be employed for the administration unit 10b. Having administered a contrast agent, the administration unit 10b outputs a control signal indicating this administration to an imaging unit 2b or the controller 6.

The time calculator 9b and the administration unit 10b repeat the above processes until they calculate the administration start time to capture time-series images of the last area and administer a contrast agent for the time-series images, respectively. Each time time-series images are captured of one area, the imaging unit 2b of this embodiment outputs the time-series images to a first pixel value transition unit 32b. The first pixel value transition unit 32b obtains first pixel value transition information in the overlapping area that overlaps the next area each time it receives the time-series images, and outputs the information thus obtained to a pixel value estimation unit 33b. The pixel value estimation unit 33b obtains pixel value estimation information in the overlapping area that overlaps the next area each time it receives the first pixel value transition information, and outputs the information thus obtained to the time calculator 9b.

Figure 9:
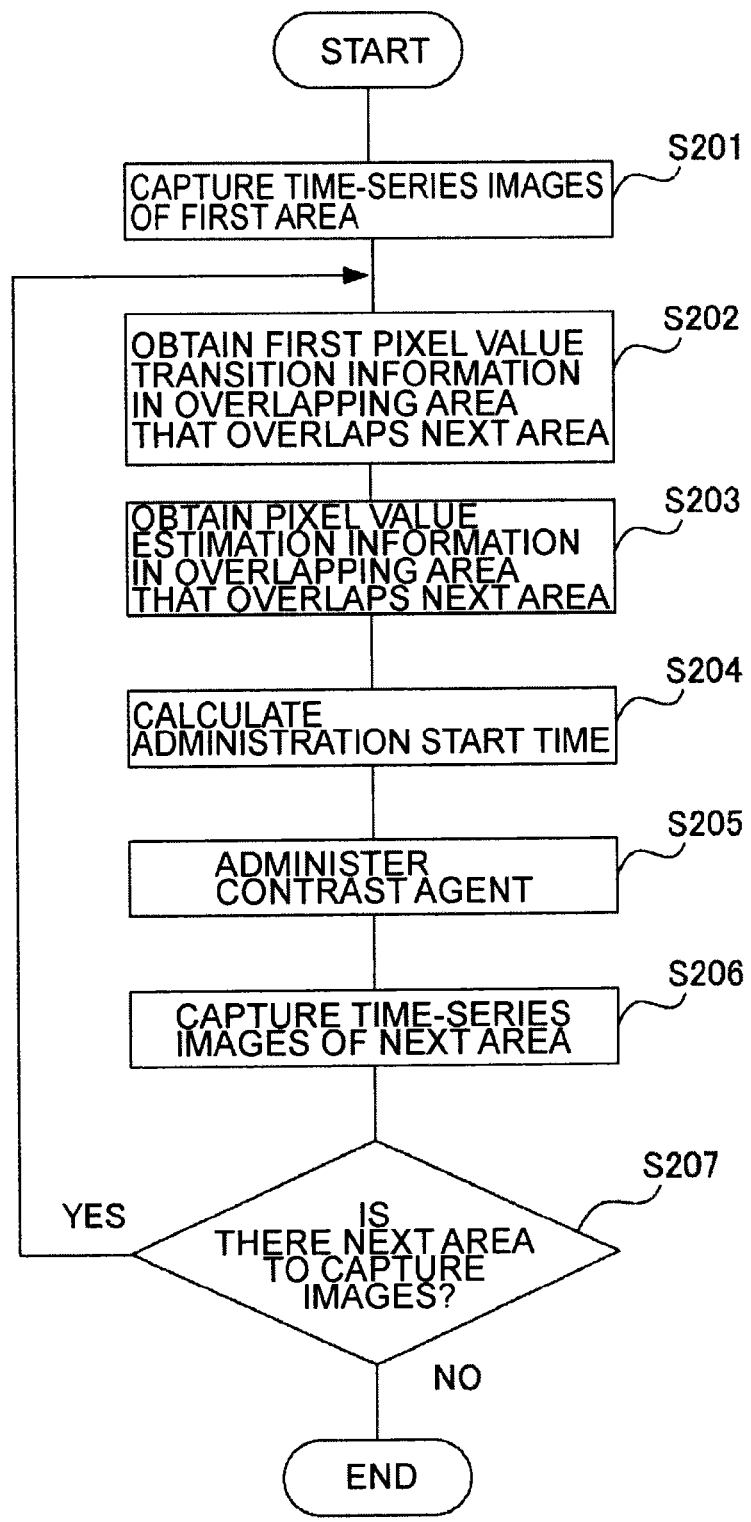
FIG. 9 is a flowchart of an example of the operation of the medical imaging analyzer of the embodiment.

The medical imaging analyzer 1b of this embodiment operates differently from that of the first embodiment in step S002 in the flowchart of FIG. 6. FIG. 9 is a detailed flowchart of step S002 in FIG. 6. Except that the operation illustrated in FIG. 9 replaces step S002, the medical imaging analyzer 1b of this embodiment operates as illustrated in FIG. 6.

S201: The imaging unit 2b captures time-series images of the first area, and outputs the captured images to the first pixel value transition unit 32b.

S202: Having received the time-series images, the first pixel value transition unit 32b obtains first pixel value transition information in the overlapping area that overlaps the next area, and outputs the first pixel value transition information to the pixel value estimation unit 33b.

S203: Having received the first pixel value transition information, the pixel value estimation unit 33b obtains pixel value estimation information in the overlapping area that overlaps the next area, and outputs the pixel value estimation information to the time calculator 9b.

S204: The time calculator 9b calculates administration start time to administer a contrast agent to capture the next time-series images. The time calculator 9b outputs the administration start time to the administration unit 10b.

S205: Having received the administration start time thus calculated, the administration unit 10b administers a contrast agent to a subject based on the administration start time.

S206: The imaging unit 2b captures time-series images of the next area, and outputs the time-series images to the first pixel value transition unit 32b.

S207: If there is still next area to capture time-series images, the process loops back to step S202. If not, the process ends.

According to the second embodiment, the medical imaging analyzer 1b further includes the time calculator 9b and the administration unit 10b. The time calculator 9b is configured to receive the pixel value estimation information each time time-series images are captured with respect to one area, and calculate administration start time to administer the contrast agent to capture next time-series images. The administration unit 10b is configured to receive the administration start time, and administer the contrast agent to the subject based on the administration start time. In this manner, the medical imaging analyzer 1b calculates the time at which the contrast agent administered for captured time-series images less remains in time-series images to be captured next, and administers a contrast agent for the next time-series images based on the calculated time. Further, the medical imaging analyzer 1b can automatically control the time to administer a contrast agent for the next time-series images based on the pixel value transition information obtained from the time-series images of one area. Thus, it is possible to further reduce the effect of residual contrast agent on images captured by moving the imaging area with a plurality of administrations of a contrast agent to perform perfusion analysis.

Third Embodiment

Figure 10:
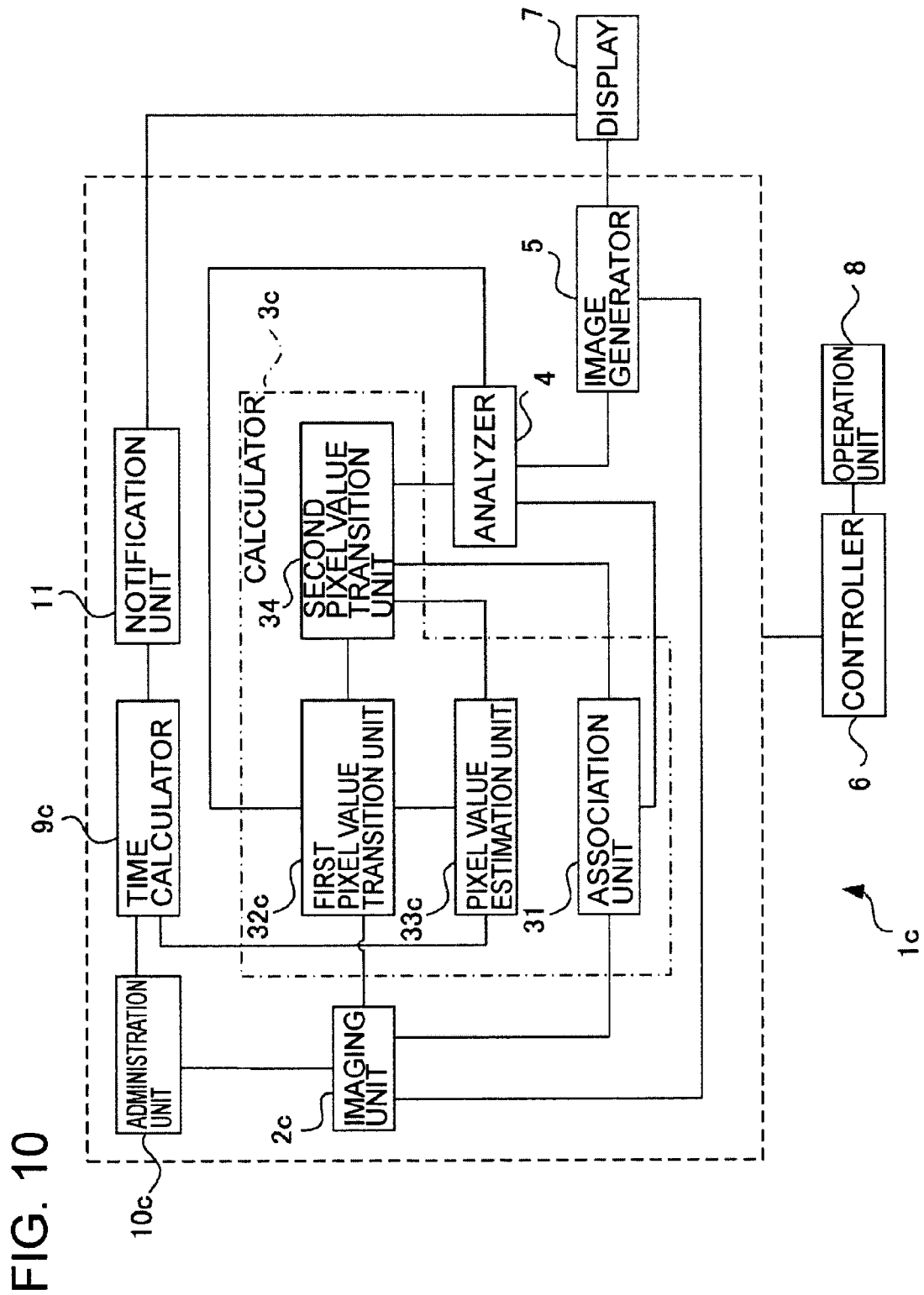
FIG. 10 is a functional block diagram illustrating a configuration of a medical imaging analyzer according to still another embodiment.

FIG. 10 is a block diagram illustrating a configuration of a medical imaging analyzer 1c of this embodiment. The medical imaging analyzer 1c of this embodiment includes, in addition to the configuration of the medical imaging analyzer 1a of the first embodiment, a time calculator 9c, an administration unit 10c, and a notification unit 11. Described below are the differences from the medical imaging analyzer 1a of the first embodiment. Besides, with respect to the time calculator 9c and the administration unit 10c, differences from those of the medical imaging analyzer 1b of the second embodiment are described.

Each time time-series images are captured with respect to one area, the time calculator 9b receives pixel value estimation information and calculates the time to start administering a contrast agent to capture the next time-series images. The time calculator 9c outputs the administration start time to the notification unit 11.

Having received the administration start time thus calculated, the notification unit 11 notifies the user of the administration start time. For example, the notification unit 11 displays the administration start time on the display 7. Thereby, the user can check the time to administer a contrast agent for the next time-series images and provide the administration unit 10c with an instruction to administer the contrast agent at that time. Alternatively, the notification unit 11 may notify the administration start time by voice or the like.

Having received the instruction to administer a contrast agent, the administration unit 10b administers a contrast agent to a subject (manual administration). This instruction is provided by the user through the operation unit 8 and the controller 6. The contrast agent administered at this time is the one to capture time-series images of the next area.

The time calculator 9b, the notification unit 11 and the administration unit 10b repeat the above processes until they calculate the administration start time to capture time-series images of the last area and administer a contrast agent for the time-series images. Each time time-series images are captured of one area, an imaging unit 2c of this embodiment outputs the time-series images to a first pixel value transition unit 32c. The first pixel value transition unit 32c obtains first pixel value transition information in the overlapping area that overlaps the next area each time it receives the time-series images, and outputs the information thus obtained to a pixel value estimation unit 33c. The pixel value estimation unit 33c obtains pixel value estimation information in the overlapping area that overlaps the next area each time it receives the first pixel value transition information, and outputs the information thus obtained to the time calculator 9c.

Figure 11:
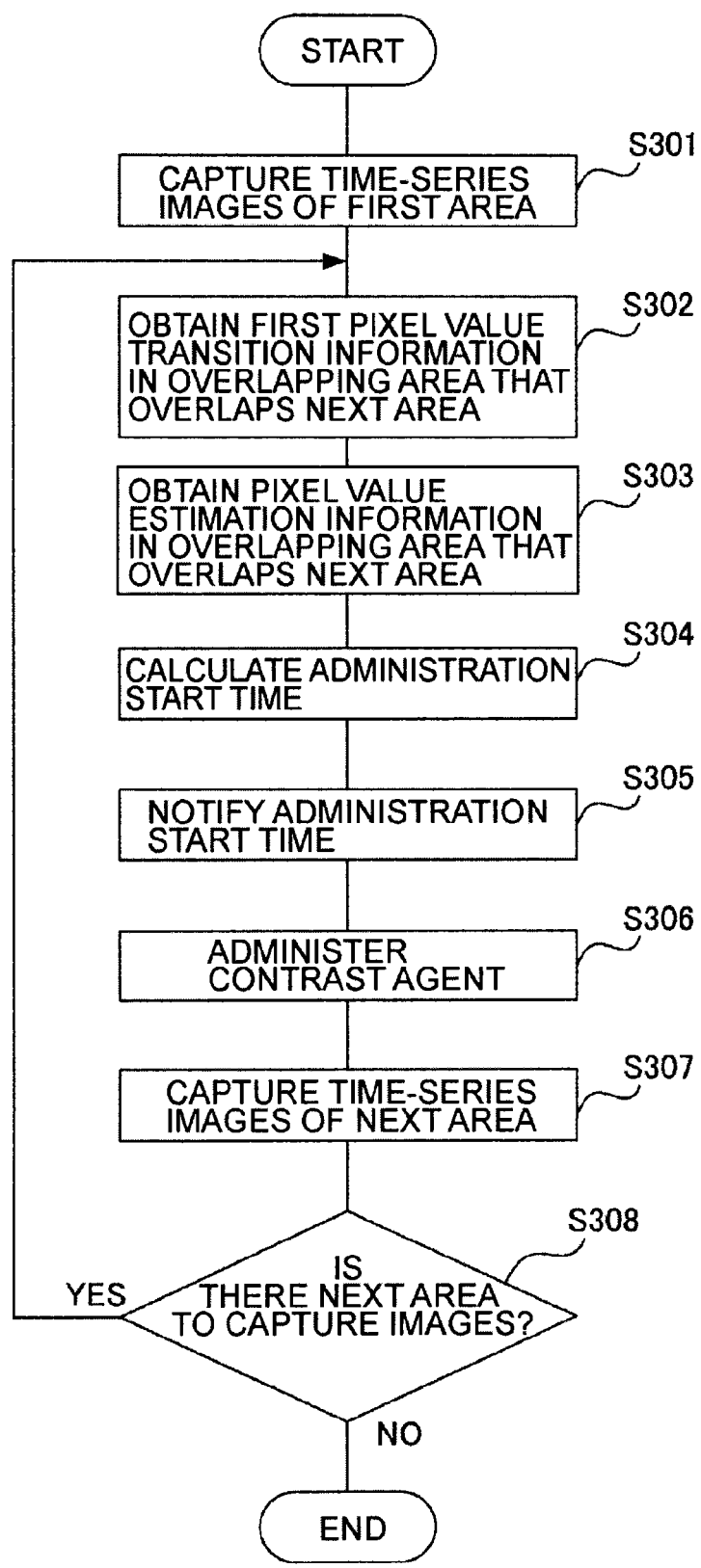
FIG. 11 is a flowchart of an example of the operation of the medical imaging analyzer of the embodiment.

The medical imaging analyzer 1c of this embodiment operates differently from that of the first embodiment in step S002 in the flowchart of FIG. 6. FIG. 11 is a detailed flowchart of step S002 in FIG. 6. Except that the operation illustrated in FIG. 11 replaces step S002, the medical imaging analyzer is of this embodiment operates as illustrated in FIG. 6.

S301: The imaging unit 2c captures time-series images of the first area, and outputs the captured images to the first pixel value transition unit 32c.

S302: Having received the time-series images, the first pixel value transition unit 32c obtains first pixel value transition information in the overlapping area that overlaps the next area, and outputs the first pixel value transition information to the pixel value estimation unit 33c.

S303: Having received the first pixel value transition information, the pixel value estimation unit 33c obtains pixel value estimation information in the overlapping area that overlaps the next area, and outputs the pixel value estimation information to the time calculator 9c.

S304: The time calculator 9c calculates administration start time to administer a contrast agent to capture the next time-series images. The time calculator 9c outputs the administration start time to the notification unit 11.

S305: Having received the administration start time thus calculated, the notification unit 11 notifies the user of the administration start time. For example, the notification unit 11 displays the administration start time on the display 7.

S306: Having received an instruction to administer a contrast agent, the administration unit 10b administers a contrast agent to a subject.

S307: The imaging unit 2c captures time-series images of the next area, and outputs the time-series images to the first pixel value transition unit 32c.

S308: If there is still next area to capture time-series images, the process loops back to step S302. If not, the process ends.

According to the third embodiment, the medical imaging analyzer 1c further includes the time calculator 9c and the notification unit 11. The time calculator 9c is configured to receive the pixel value estimation information each time time-series images are captured with respect to one area, and calculate administration start time to administer the contrast agent to capture next time-series images. The notification unit 11 is configured to receive the administration start time, and notify the administration start time. In this manner, the medical imaging analyzer 1c calculates the time at which the contrast agent administered for captured time-series images less remains in time-series images to be captured next, and administers a contrast agent for the next time-series images based on the calculated time. Further, the medical imaging analyzer 1c notifies the user of the time to administer a contrast agent for the next time-series images based on the pixel value transition information obtained from the time-series images of one area. Thus, it is possible to further reduce the effect of residual contrast agent on images captured by moving the imaging area with a plurality of administrations of a contrast agent to perform perfusion analysis.

According to at least one of the embodiments described above, the medical imaging analyzer includes the association unit, the first pixel value transition unit, the pixel value estimation unit, and the second pixel value transition unit. This configuration enables to reduce the difference in the shape and size of the organ to be rendered in images captured by moving the imaging area with a plurality of administrations of a contrast agent as well as to reduce the effect of residual contrast agent. Thus, it is possible to perform perfusion analysis on an image in which an artery area is not specified.

A medical image processing method for realizing the above embodiments may be implemented by a computer program stored in a recording medium readable by a computer. Examples of the recording medium include semiconductor memories, optical disks, magneto-optical disks, magnetic storage media, and the like. The program may be sent/received through a network such as the Internet or LAN.

Although the perfusion analysis is described herein as being applied to the lungs, this is by way of example only. The embodiments are not limited to this, and can be applicable to the brain, heart, kidney, liver, small intestine, large intestine, and other organs.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical imaging analyzer comprising processing circuitry configured to:
    divide an area including an object of a subject to be captured into a plurality of partial areas such that the partial areas overlap each other to form an overlapping area, and administer a contrast agent to each of the partial areas to capture a plurality of time-series images;
    calculate, based on a transition in pixel value in one of the time-series images having the overlapping area, a transition in pixel value in another of the time-series images having the overlapping area; and
    analyze the time-series images based on the transition in pixel value in the one and the other of the time-series images to obtain hemodynamics of the subject.

2. The medical imaging analyzer of claim 1, wherein the processing circuitry is further configured to:
    obtain a correspondence relationship between the one and the other of the time-series images to perform registration between the one and the other of the time-series images;
    obtain first pixel value transition information that represents a transition in pixel value in the time-series images as the transition in pixel value in the one of the time-series images;
    obtain pixel value estimation information in the overlapping area, wherein the pixel value estimation information is information that, regarding capturing time of second and subsequent time-series images among the time-series images related to the first pixel value transition information, estimates a transition in pixel value due to a change in concentration of the contrast agent administered for capturing a previous time-series image; and
    obtain second pixel value transition information that represents a transition in pixel value depending on the concentration of the contrast agent administered to capture each of the time-series images.

3. The medical imaging analyzer of claim 2, wherein the processing circuitry is further configured to compare an image in the overlapping area of the one of the time-series images with an image in the overlapping area of the other of the time-series images to obtain the correspondence relationship, and perform registration between the one and the other of the time-series images to constitute a target site, which is the object to be captured.

4. The medical imaging analyzer of claim 3, wherein the processing circuitry is further configured to
acquire an entire area image that represents an entire area of the object to be captured, and
compare the one of the time-series images with the entire area image and compare the other of the time-series images with the entire area image to obtain the correspondence relationship, and perform registration between the one and the other of the time-series images based on the correspondence relationship to constitute the entire area image.

5. The medical imaging analyzer of claim 2, wherein the processing circuitry is further configured to obtain the second pixel value transition information of a time-series image captured later in the time-series images having the overlapping area, based on the pixel value estimation information and the first pixel value transition information of the time-series image captured later, and the correspondence relationship between the time-series image captured later and a time-series image captured first.

6. The medical imaging analyzer of claim 5, wherein the processing circuitry is further configured to subtract a value obtained by multiplying a pixel value represented by the pixel value estimation information of the time-series image captured later by a weighting factor with respect to each time point, from a pixel value represented by the first pixel value transition information of the time-series image captured later to obtain the second pixel value transition information.

7. The medical imaging analyzer of claim 2, wherein the processing circuitry is further configured to
obtain the hemodynamics of the subject for each of the time-series images, and
perform weighted addition of the hemodynamics of the one and the other of the time-series images having the overlapping area based on the hemodynamics obtained and the correspondence relationship.

8. The medical imaging analyzer of claim 2, wherein the processing circuitry is further configured to obtain, as the correspondence relationship, a relationship of either or both of anatomical location and scale of organ of the subject rendered in the overlapping area between the one and the other of the time-series images.

9. The medical imaging analyzer of claim 2, wherein the processing circuitry is further configured to
calculate administration start time to administer the contrast agent to capture next time-series images each time the pixel value estimation information is obtained for time-series images captured with respect to one area, and
administer the contrast agent to the subject based on the administration start time.

10. The medical imaging analyzer of claim 2, wherein the processing circuitry is further configured to
calculate administration start time to administer the contrast agent to capture next time-series images each time the pixel value estimation information is obtained for time-series images captured with respect to one area, and
notify the administration start time calculated.

11. A medical image processing method comprising:
capturing a plurality of time-series images of a plurality of partial areas by administering a contrast agent to each of the partial areas, the partial areas being obtained by dividing an area including an object of a subject to be captured such that the partial areas overlap each other to form an overlapping area;
calculating, based on a transition in pixel value in one of the time-series images having the overlapping area, a transition in pixel value in another of the time-series images having the overlapping area; and
analyzing the time-series images based on the transition in pixel value in the one and the other of the time-series images to obtain hemodynamics of the subject.

* * * * *